United States Patent [19] [11] 4,256,890
Nakagawa et al. [45] * Mar. 17, 1981

[54] 3,4-DIHYDROCARBOSTYRIL DERIVATIVES AND PROCESS FOR PRODUCING THE SAME

[75] Inventors: Kazuyuki Nakagawa; Nanami Murakami, both of Tokushima; Shiro Yoshizaki, Komatsujima; Hideo Mori; Michiaki Tominaga, both of Tokushima, all of Japan

[73] Assignee: OtsukaPharmaceutical Co., Ltd., Tokyo, Japan

[*] Notice: The portion of the term of this patent subsequent to Oct. 7, 1992, has been disclaimed.

[21] Appl. No.: 886,373

[22] Filed: Mar. 14, 1978

Related U.S. Application Data

[63] Continuation of Ser. No. 601,569, Aug. 1, 1975, abandoned, which is a continuation of Ser. No. 325,591, Jan. 23, 1973, abandoned.

[30] Foreign Application Priority Data

Sep. 14, 1972 [JP] Japan .................................. 47-92558
Sep. 14, 1972 [JP] Japan .................................. 47-92560
Dec. 2, 1972 [JP] Japan .................................. 47-120953
Dec. 2, 1972 [JP] Japan .................................. 47-125858
Dec. 2, 1972 [JP] Japan .................................. 47-128972
Dec. 14, 1972 [JP] Japan .................................. 47-92557

[51] Int. Cl.³ ........................................ C07D 215/22
[52] U.S. Cl. .................................... 546/158; 544/128; 544/363
[58] Field of Search ................. 544/363, 128; 546/158

[56] References Cited

U.S. PATENT DOCUMENTS 3,910,924  10/1975  Tamura et al. .................. 260/288 R Primary Examiner—Paul M. Coughlan, Jr.
Attorney, Agent, or Firm—Sughrue, Rothwell, Mion, Zinn and Macpeak

[57] ABSTRACT

Novel compounds represented by the formula

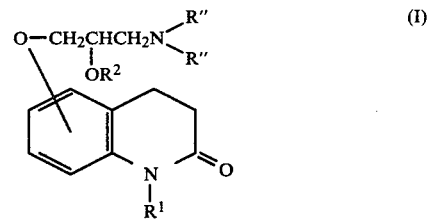

wherein $R^1$, $R^2$, and $R'$ and $R''$ are defined as hereinafter, having a blocking activity on $\beta$-adrenergic nerves, novel intermediates useful for synthesis thereof and processes for preparing the same are disclosed. When substitution is at the 5-position and $R^1$ and $R^2$ are hydrogen, $R'$ and $R''$ are not simultaneously hydrogen and a 1 to 4 carbon atom alkyl group in the claimed compound.

22 Claims, No Drawings

3,4-DIHYDROCARBOSTYRIL DERIVATIVES AND PROCESS FOR PRODUCING THE SAME

This is a continuation of application Ser. No. 601,569, filed Aug. 1, 1975, in turn a continuation application of Ser. No. 325,591, filed Jan. 23, 1973, both abandoned.

BACKGROUND OF THE INVENTION

1. Field of the Invention

The present invention relates to 3,4-dihydrocarbostyril derivatives, intermediates therefor and processes of preparing the same.

2. Description of the Prior Art

It is known that certain carbostyril derivatives exhibit useful pharmacological activities. Representative compounds of this type are those disclosed in Japanese Patent Publication Nos. 1182/1967 and 38789/1971, and Chemical Abstracts, 62, 1b 212e (1965), etc. However, the above references do not teach that compounds having a 3-substituted-aminopropoxy group at 5-, 6-, 7- or 8-position of the carbostyril moiety exhibit an excellent blocking activity on β-adrenergic nerves.

SUMMARY OF THE INVENTION

This invention relates to novel 3,4-dihydrocarbostyril derivatives represented by the formula

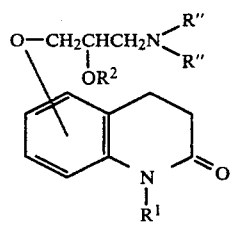

wherein $R^1$ is selected from the group consisting of a hydrogen atom, a straight or branched alkyl group having 1 to 4 carbon atoms, an aralkyl group and an alkenyl group having 2 to 4 carbon atoms, $R^2$ is selected from the group consisting of a hydrogen atom and an acyl group of the formula $COR^3$ wherein $R^3$ represents a lower alkyl group having 1 to 4 carbon atoms, a phenyl group or a 3,4,5-trimethoxyphenyl group, and R' and R'' may be the same or different and each represents a hydrogen atom, a lower alkyl group having 1 to 4 carbon atoms, an aralkyl group such as a phenyl alkyl group with 1 to 4 carbon atoms in the alkyl group or a cycloalkyl group of 4 to 6 carbon atoms, or R' and R'', when taken together with the nitrogen atom to which they are attached, may form a heterocyclic group with 2 to 8 carbon atoms which may contain an additional nitrogen atom or an oxygen atom as a ring member, and acid addition salts of the above 3,4-dihydrocarbostyril derivatives and novel intermediates useful for the preparation of the compounds of the formula (I) as well as the processes for preparing the compounds of the formula (I) and the intermediates.

When substitution is at the 5-position, R' and R'' are not simultaneously hydrogen and a 1 to 4 carbon atom alkyl group in the claimed compound. The processes described, however, include the method of making such materials.

DETAILED DESCRIPTION OF THE INVENTION

The novel 3,4-dihydrocarbostyril derivatives and the intermediates therefor can be prepared by the following reaction scheme:

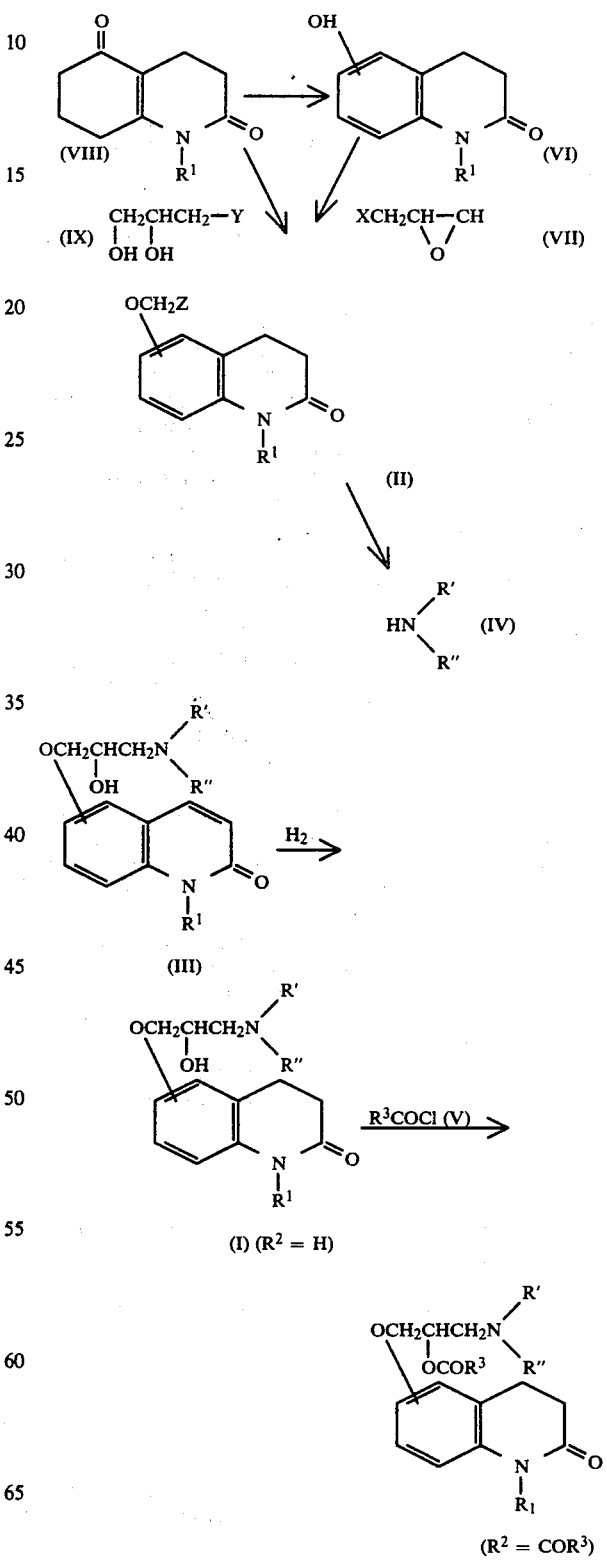

wherein $R^1$, $R^2$, $R^3$, $R'$ and $R''$ are as defined above, X is halogen (F, Br, Cl, I), Y and Z are defined hereinafter.

The novel intermediates of this invention are represented by the formula

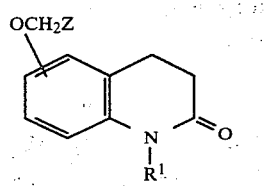

wherein $R_1$ is as defined above, and Z represents a group of the formula

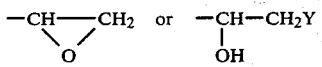

wherein Y represents a halogen atom.

5-(3-Amino-2-substituted)propoxy-3,4-dihydrocarbostyril derivatives (I) of this invention are basic substances and can form acid addition salts with various acids, for example, inorganic acids such as hydrochloric, sulfuric and phosphoric acids and organic acids such as oxalic, maleic, fumaric, malic, tartaric, citric and ascorbic acid and the like. These acid addition salts are preferably prepared by any well known procedure for producing acid addition salts, for example, by separately dissolving the basic compound and an appropriate acid in an organic solvent such as acetone and combining the solutions in stoichiometrical proportions. The acid addition salts illustrate increased solubility in water as compared to the free base form, and increased stability to heat and light. Any pharmaceutically acceptable acid addition salt may be used.

Both the above free bases and acid addition salts thereof exhibit a blocking activity on β-adrenergic nerves and therefor are useful as pharmaceuticals for treating arhythmia in auricular fibrillation and disorders in coronary sclerosis such as arrhythmias, tachycardia, angina pectoris, coronary insufficiency, hypertension, etc.

The term "lower alkyl" used throughout the specification and claims means a straight or branched chain alkyl group having 1 to 4 carbon atoms including methyl, ethyl, n-propyl, isopropyl, n-butyl, sec.-butyl and tert.-butyl.

The term "aralkyl" means an unsubstituted phenylalkyl group having 1 to 4 carbon atoms in the alkyl moiety, for example, a benzyl group.

The term "alkenyl" means a straight or branched alkenyl group having 2 to 4 carbon atoms, for example, an allyl group.

The term "cycloalkyl" means a cycloalkyl group having 4 to 6 carbon atoms, i.e., cyclobutyl, cyclopentyl and cyclohexyl groups.

Examples of the heterocyclic group of the formula

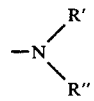

include piperidino, piperazino and morpholino, each of which may be substituted with an alkyl group having 1 to 4 carbon atoms. When substitution is at the 5-position, $R'$ and $R''$ are not simultaneously hydrogen and a 1 to 4 carbon atom alkyl group in the claimed compound. The processes described, however, include the method of making such materials.

The compound of this invention having the formula (I) wherein $R^2$ represents a hydrogen atom can be prepared by either of two alternative processes. The first process comprises reacting a 5-hydroxy-3,4-dihydrocarbostyril derivative of the formula (II) with a secondary or tertiary amine of the formula

wherein $R'$ and $R''$ are as defined above.

The reaction between the 3,4-dihydrocarbostyril derivatives of the formula (II) and the amine of the formula (IV) can be carried out in the absence of solvents but is advantageously carried out in the presence of an inert organic solvent. Suitable examples of the solvent are lower alkyl ethers such as diethyl ether, methyl ethyl ether, dipropyl ether, other ethers such as dioxane and tetrahydrofuran, hydrocarbons such as benzene, toluene, xylene, and the like, lower alkanols such as methanol, ethanol, propanol, iso-propanol, n-butanol, and the like, water, dialkylformamides such as dimethylformamide, diethylformamide and the like. The most preferred solvents are methanol, ethanol, tetrahydrofuran, dioxane, benzene, toluene, dimethylformamide. With a subgroup of preferred solvents being the polar solvents such as methanol, ethanol and the like.

In carrying out the reaction, the amine can generally be used in an equimolar proportion to a molar excess, but preferably is used in a proportion of from 6 to 8 moles per 1 mole of 3,4-dihydrocarbostyril derivative (II). The reaction temperature is not critical and the reaction proceeds smoothly at a temperature between room temperature and a boiling point of the solvent used. The preferred temperature ranges from 40° to 60° C. whether or not a solvent is used. In particular, the reaction can advantageously be carried out at the boiling point of the solvent when a heterocyclic amine is used as the amine reactant (III). The reaction is normally carried out at atmospheric pressure, but the reaction may be carried out under pressurized conditions in the range of 1 atms. to 10 atms. The reaction time varies depending upon the reaction temperature used, but the reaction is completed within 3 to 8 hours, generally within 4 to 5 hours. The resulting product can be isolated by conventional procedures, for example, by filtration or removal of the solvent from the reaction mixture by distillation and can be purified by conventional procedures, for example, by recrystallization from an appropriate solvent.

A second process for preparing the compound of formula (I) wherein $R^2$ represents a hydrogen atom comprises reducing the corresponding (2-hydroxy-3-alkylamino)propoxycarbostyril of the formula

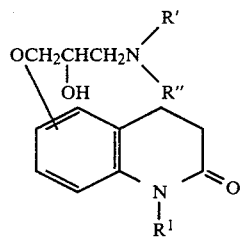

wherein $R^1$, $R'$ and $R''$ are as defined above. The reduction is conducted using hydrogen in the presence of a noble metal catalyst generally employed in hydrogenation of organic compounds, for example, Raney nickel, palladium black, platinum oxide, platinum black etc., in an organic solvent at a temperature of from room temperature to an elevated temperature in the range of from 0° to 150° C., preferably from 50° to 70° C. under normal hydrogen pressure or pressurized conditions in the range of from 1 to 200 atms., preferably from 10 to 50 atms. The pressure somewhat varies depending upon the type of the catalyst used. When palladium-on-carbon is used, a preferred pressure range is from 2 to 10 atms. and when nickel is used a preferred pressure range is from 50 to 150 atms. Suitable solvents are halogenated carbons and mixtures of halogenated carbons and lower alkanols such as chloroform, carbon tetrachloride, dichloroethane, a mixture of methanol and chloroform, and a mixture of ethanol and carbon tetrachloride and the like. The most preferred solvents are chloroform and carbon tetrachloride. Any organic solvent which is inert to the reactants and the product can be used in the reduction. Examples of the solvent are lower alkanols such as methanol, ethanol and the like, glacial acetic acid, ethyl acetate and the like.

The 5-(2-hydroxy-3-alkylamino)propoxycarbostyrils are also basic compounds and can form acid addition salts as set forth for the acid addition salts of the compounds having formula (I). The above described reduction can also be carried out using acid addition salts of the compounds of formula (III) under the same conditions as described for the free base (III). The compounds of the formula (III) are novel compounds and exhibit the same physiological activities as the compounds of formula (I). These compounds (III) can easily be synthesized according to the following reaction scheme:

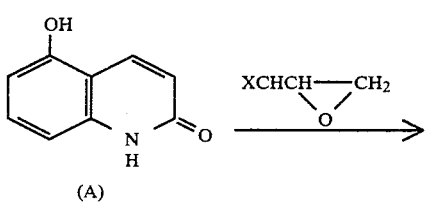

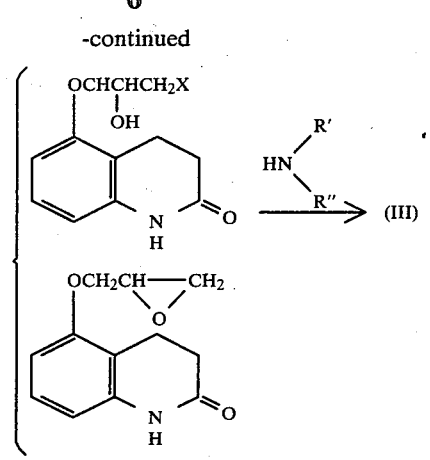

wherein X, $R'$ and $R''$ are as defined above. The starting compound (A) used in the above reaction is disclosed in W. C. Fleming and G. R. Pettit, J. Org. Chem., 36 (23), 3490–3493 (1971).

The compounds of the formula (I) wherein $R^2$ represents an acyl group of the formula $COR^3$, wherein $R^3$ is as defined above, can be prepared from the corresponding compounds of formula (I) wherein $R^2$ represents hydrogen by acylation using an appropriate acylating agent. This acylation can advantageously be carried out using an acyl chloride of the formula $$R^3COCl \qquad (V)$$

wherein $R^3$ is as defined above. The acylation may be conducted in the absence of solvents, but advantageously is carried out in the presence of an inert organic solvent, for examples, dialkyl ethers such as diethyl ether, dipropyl ether, methylethyl ether, other ethers such as dioxane, tetrahydrofuran and the like, hydrocarbons such as benzene, toluene, xylene, and the like, ketones such as acetone, methylethyl ketone, dialkylformamides such as dimethylformamide, diethylformamide, and the like. Preferred solvents are acetone, toluene, xylene and benzene.

The acylation generally proceeds smoothly without using acid acceptors for hydrochloric acid formed during the acylation, but better results seem to be obtained in the presence of acid acceptors. Suitable examples of acid acceptors are alkali metal hydrides such as sodium hydride, potassium hydride and the like, alkali metal hydroxides such as sodium hydroxide, potassium hydroxide and the like, alkali metal carbonates such as sodium carbonate, potassium carbonate and the like, organic bases such as piperidine, piperazine, pyridine, lower alkylamines, e.g., diethylamine, triethylamine, methylamine and the like. The acyl chloride of the formula (V) is used in a proportion of from an equimolar to molar excess amount with respect of (2-hydroxy-3-amino)propoxy-3,4-dihydrocarbostyril derivatives to be acylated, but generally the acyl chloride is used in an amount of from 3 to 5 moles per 1 mole of the (2-hydroxy-3-amino)propoxy-3,4-dihydrocarbostyril derivatives. The temperature for acylation is not critical and can range from room temperature to the boiling point of the solvent, if used. Best results are generally obtained by conducting the acylation in the presence of an appropriate solvent while maintaining the reaction mixture at the boiling point of the solvent. The reaction is generally completed in 3 to 6 hours, preferably 4 to 5 hours.

As described previously, the present invention involves the novel intermediates represented by formulae (II) and (III).

The novel intermediates of the formula (II) can easily be prepared by reacting the corresponding 5-(or 6-, 7- or 8-)hydroxy-3,4-dihydrocarbostyril derivative of the formula

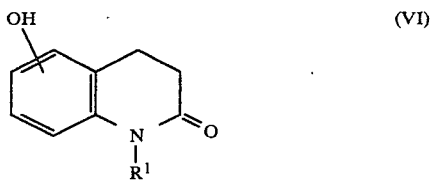

wherein $R^1$ is as defined above, with an epihalohydrin of the formula

wherein X is as defined above, in the presence of a basic compound. Usually from 1 to 10 moles of epihalohydrin, preferably from 1 to 3 moles, is used per mole of the compound of formula (VI). The starting compounds of the formula (VI) are known compounds and disclosed in Japanese Patent Publication Nos. 39694/1971 and 38789/1971. Reference can also be made to Fritz Mayer, Berichte 60, 858–862 (1927) as to the preparation of 6-, 7- and 8-hydroxy compounds of the formula (VI).

More specifically, 5-hydroxy-3,4-dihydrocarbostyril derivatives which are representative compounds of formula (VI) can be prepared from 3,4,5,6,7,8-hexahydrocarbostyril-5-one by reacting the same with a brominating agent to obtain the corresponding 8(or 6)-bromo-3,4,5,6,7,8-hexahydrocarbostyril-5-one which is then subjected to heat treatment according to the following reaction scheme:

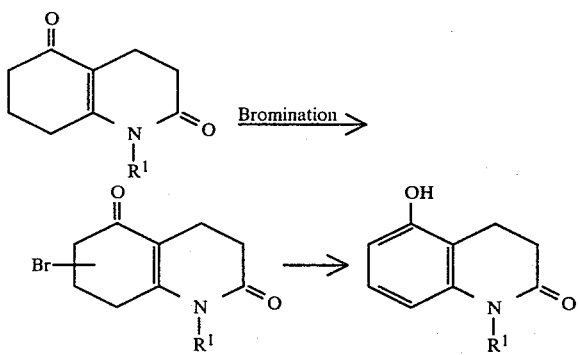

Suitable examples of the epihalohydrin are epibromohydrin, epichlorohydrin or epiiodohydrin. Suitable basic compounds are alkali metals, alkali hydroxides, alkali carbonates and organic bases. Preferred examples of the basic compounds are sodium metal, potassium metal, sodium hydroxide, potassium hydroxide, sodium carbonate, potassium carbonate, piperidine, piperazine, pyridine, lower alkylamines such as diethylamine, triethylamine, methylamine and the like. The reaction between compounds (VI) and (VII) can be carried out in the absence of solvents, but preferably carried out in the presence of an inert solvent, for example, lower alkanols, water, lower alkyl acetate and ketones. Suitable examples of lower alkanols are methanol, ethanol, isopropanol, n-propanol, n-butanol and the like. Suitable examples of lower alkyl acetates are ethyl acetate, methyl acetate, propyl acetate, and the like. Suitable examples of ketones are acetone and methyl ethyl ketone. Although any combination of the solvent and basic compound can be used, it is preferred to select the solvent depending upon the basic compound used. In preferred embodiments, lower alkanols are used with alkali metals and water with alkali hydroxides. When the basic compounds are organic bases the reaction can be carried out without using any solvent or with a lower alkanol, lower alkyl acetate or ketone.

The reaction temperature can range from 0° to the boiling point of the solvent used, preferably from 50° to a boiling point of the solvent for a period of from 4 to 6 hours, preferably from 4 to 5 hours when alkali metals or alkali hydroxides are used as the basic compound, and the reaction temperature can range from 0° to 120° C., preferably 80° to 120° C. for a period of from 4 to 6 hours, preferably 5 to 6 hours, when organic bases are used as the basic compound. The reaction is usually carried out at atmospheric pressure. In this reaction, both 5(or 6, 7 or 8)-(2,3-epoxy)propoxy-3,4-dihydrocarbostyril derivatives and 5(or 6, 7 or 8)-(2-hydroxy-3-halogeno)propoxy-3,4-dihydrocarbostyril derivatives (formula (II) wherein Y is

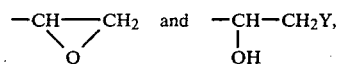

(respectively) are obtained as a reaction product. The proportion of the products (I) and (II) varies with the type of the basic compounds used. The former compound (I) is produced predominantly when the reaction is conducted in the presence of strongly basic compounds such as alkali metals and alkali hydroxides as recited above and the latter compound is produced predominantly when the reaction is conducted in the presence of a weakly basic compounds such as organic bases, in particular piperidine and the epihalohydrin is used in excess.

These products can be separated from each other by conventional procedures, for example, fractional crystallization, but preferably are separated by column chromatography using a column packed with active alumina, silica gel or the like.

The intermediate of formula (II) wherein Z represents

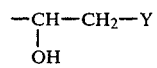

(Y is as defined above) can also be prepared by reacting a 5-hydroxy-3,4-dihydrocarbostyril derivative of the formula

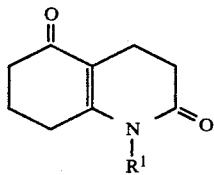

(VIII)

wherein R¹ is as defined above, with a 3-halogeno-1,2-propanediol of the formula

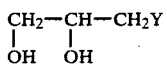

(IX)

wherein Y is as defined above. It is preferred to react 1 to 5 moles of the compound of formula (IX), more preferably 1 to 3 moles, per mole of the compound of formula (VIII). This reaction is carried out at atmospheric pressure for 3 to 6 hours, preferably 4 to 5 hours, in the presence of a brominating agent such as pyridinium bromide, perbromide or bromine in an inert solvent which does not take part in the reaction such as carbon tetrachloride at a temperature in the range of from room temperature to a boiling point of the solvent, preferably at or near the boiling point of the solvent used. Suitable solvents are halogenated carbons and mixtures of halogenated carbons and lower alkanols such as chloroform, carbon tetrachloride, dichloroethane, a mixture of methanol and chloroform, and a mixture of ethanol and carbon tetrachloride and the like. The most preferred solvents are chloroform and carbon tetrachloride. The compounds of the formula (VIII) are well known in the art and disclosed in E. H. W. Böhme It is preferred to use to moles of brominating agent, more preferably to moles, per one mole of the compound of formula (VIII).

This invention will now be further illustrated by way of several examples, but they are not to be construed as limiting the present invention.

EXAMPLE 1

Preparation of Compound of Formula II 1.53 g of 5-hydroxy-3,4-dihydrocarbostyril and 3.5 g of epichlorohydrin were added to 30 ml of a methanolic solution of 0.216 g of sodium metal and the resulting solution was stirred at a temperature of from 55° to 60° C. for 4 hours. After allowing the solution to cool, the precipitated sodium chloride was filtered and the filtrate was concentrated to dryness under reduced pressure. To the resulting residue was added acetone to crystallize the product. Recrystallization of the product from ethanol gave 0.8 g of 5-(2,3-epoxy)propoxy-3,4-dihydrocarbostyril having a melting point of 172°–173° C. as a colorless amorphous solid. A solution of the filtrate in acetone was concentrated to dryness and the resulting residue was recrystallized from ethyl acetate to give 0.05 g of 5-(2-hydroxy-3-chloro)propoxy-3,4-dihydrocarbostyril having a melting point of 157°–158° C. as a colorless amorphous solid.

EXAMPLE 2

Preparation of Compound of Formula II

To a solution of 0.6 g of sodium hydroxide dissolved in 40 ml of water were added 2.5 g of 5-hydroxy-3,4-dihydrocarbostyril and 3.0 g of epibromohydrin, and the resulting solution was stirred at a temperature of from 60° to 65° C. for 4 hours. After allowing the solution to cool, the precipitated crystals were separated by filtration and recrystallized from ethanol to give 1.9 g of 5-(2,3-epoxy)propoxy-3,4-dihydrocarbostyril having a melting point of 172°–173° C.

EXAMPLE 3

Preparation of Compound of Formula II 4.7 g of epichlorohydrin and 3 drops of piperidine were added to 5.1 g of 1-benzyl-5-hydroxy-3,4-dihydrocarbostyril, and the resulting mixture was stirred for 5 hours at a temperature of from 95° to 100° C. The reaction mixture was then concentrated to dryness, and the residue was dissolved in 60 ml of chlorofrom. The solution thus obtained was washed successively with a 5% aqueous sodium hydroxide solution and water and dried over anhydrous sodium sulfate. The dried solution was then passed through a chromatography column filled with active alumina and the column was developed with chloroform. The first eluate containing 1-benzyl-5-(2,3-epoxy)propoxy-3,4-dihydrocarbostyril was concentrated to dryness and the residue was recrystallized from ethanol to give 0.5 g of the above product having a melting point of 120° to 122° C. as colorless amorphous crystals. The subsequent eluate containing 1-benzyl-5-(2-hydroxy-3-chloro)propoxy-3,4-dihydrocarbostyril was concentrated to dryness, and the residue was recrystallized from carbon tetrachloride to give 3.2 g of the above product having a melting point of 105° to 107° C. as a colorless amorphous crystals.

EXAMPLE 4

Preparation of Compound of Formula II 3.8 g of epibromohydrin and 3 drops of piperidine were added to 3.0 g of 1-ethyl-5-hydroxy-3,4-dihydrocarbostyril, and the mixture was stirred for 5 hours at a temperature of from 95° to 100° C. The reaction mixture was then concentrated to dryness and the residue was dissolved in 10 ml of acetone. After addition of 10 ml of ether and 20 ml of benzene, the solution was poured into a chromatography column packed with silica gel and the column was developed with a solvent system consisting of acetone:ether:benzene (1:1:2). The first eluate was concentrated to dryness, and the residue was crystallized from n-hexane to give 0.3 g of 1-ethyl-5-(2,3-epoxy)propoxy-3,4-dihydrocarbostyril having a melting point of 50°–52.5° C. as colorless amorphous crystals. The subsequent eluate containing 1-ethyl-5-(2-hydroxy-3-bromo)propoxy-3,4-dihydrocarbostyril was concentrated to dryness and the residue was recrystallized from carbon tetrachloride to give 1.9 g of the above product having a melting point of 115°–117.5° C. as colorless amorphous crystals.

EXAMPLE 5

Preparation of Compound of Formula II 4.2 g of epibromohydrin and 3 drops of piperidine were added to 2.5 g of 1-allyl-5-hydroxy-3,4-dihydrocarbostyril. After allowing the mixture to react, the reaction mixture was worked up in the same manner as described in Example 4 and chromatographed using the same chromatography column as was used in Example 4. The first eluate from the column was concentrated to give crude 1-allyl-5-(2,3-epoxy)propoxy-3,4-dihydrocarbostyril. Recrystallization from carbon tetrachloride yielded 0.4 g of the same product having a melting point of 73.5°–75.0° C. as colorless amorphous crystals. The subsequent eluate was concentrated to give crude 1-allyl-5-(2-hydroxy-3-bromo)propoxy-3,4-dihydrocarbostyril. Recrystallization from carbon tetrachloride yielded 1.7 g of the same product having a melting point of 82°–84° C. as colorless amorphous crystals.

In the same manner as described in Example 4, the following compound were prepared:

1-allyl-5-(2-hydroxy-3-chloro)propoxy-3,4-dihydrocarbostyril, m.p., 65°–67° C. (recrystallized from carbon tetrachloride), 1-ethyl-5-(2-hydroxy-3-chloro)propoxy-3,4-dihydrocarbostyril, m.p., 65°–67° C. (recrystallized from carbon tetrachloride), 5-(2-hydroxy-3-chloro)propoxy-1-methyl-3,4-dihydrocarbostyril, m.p., 117°–119° C. (recrystallized from carbon tetrachloride), 5-(2-hydroxy-3-bromo)propoxy-1-methyl-3,4-dihydrocarbostyril, m.p., 137°–139° C. (recrystallized from carbon tetrachloride), 5-(2,3-epoxy)propoxy-1-methyl-3,4-dihydrocarbostyril, m.p., 76°–78° C. (recrystallized from carbon tetrachloride-n-hexane), and 5-(2-hydroxy-3-bromo)propoxy-3,4-dihydrocarbostyril, m.p., 133°–135° C. (recrystallized from ethyl ether).

EXAMPLE 6

Preparation of Compound of Formula II 5.5 g of 3-chloro-1,2-propanediol was added to a solution of 8.3 g of 3,4,5,6,7,8-hexahydrocarbostyril-5-one in 70 ml of chloroform, followed by the addition of 8.9 g of N-bromosuccinimide. The mixture was then heated at reflux for 2 hours on a water bath. After allowing the mixture to cool, 50 ml of water was added thereto and the precipitated crystals were filtered off and the chloroform layer was separated. The chloroform layer was washed successively with a 5% aqueous sodium hydroxide solution and anhydrous sodium sulfate. The dried chloroform solution was concentrated under reduced pressure, and ether was added to the resulting residue to crystallize the product. Recrystallization of the product from ethyl acetate yielded 2.8 g of 5-(2-hydroxy-3-chloro)propoxy-3,4-dihydrocarbostyril having a melting point of 157°–158° C. as colorless amorphous crystals.

EXAMPLE 7

Preparation of Compound of Formula II

A solution of 3.6 g of bromine in 50 ml of carbon tetrachloride was added, while stirring under ice-cooling, to a solution of 4.0 g of 3,4,5,6,7,8-hexahydrocarbostyril-5-one in 50 ml of carbon tetrachloride. After allowing the mixture to stand for one minute, the precipitate formed was removed by decantation. The carbon tetrachloride layer was distilled at room temperature to remove the solvent (CCl4), and the resulting crystals were combined with the above precipitate followed by being washed with acetone to give quantitatively 8-(or 6-) bromo-3,4,5,6,7,8-hexahydrocarbostyril-5-one having a melting point of 126°–127° C. as yellow crystals. The thus obtained crystals were dissolved in 80 ml of carbon tetrachloride, and 3.0 g of 3-chloro-1,2-propanediol and 1.5 g of 2,4,6-tribromophenol were added to the solution. The mixture was heated at reflux for 2 hours and thereafter worked up in the same manner as described in Example 6 to give 2.1 g of 5-(2-hydroxy-3-chloro)propoxy-3,4-dihydrocarbostyril having a melting point of 157°–158° C. as colorless amorphous crystals.

EXAMPLE 8

Preparation of Compound of Formula II

To a solution of 40 g of 1-methyl-3,4,5,6,7,8-hexahydrocarbostyril-5-one dissolved in 50 ml of chloroform was added 6.6 g of 3-bromo-1,2-propanediol followed by addition of 40 g of N-bromosuccinimide, and the resulting mixture was heated at reflux for 2 hours. After allowing the mixture to cool, the mixture was washed successively with a 5% aqueous sodium hydroxide solution and a saturated aqueous sodium chloride solution, and then dried over anhydrous sodium sulfate. The dried chloroform solution was concentrated under reduced pressure, and carbon tetrachloride was added to the resulting residue to crystallize the product. Recrystallization of the product from carbon tetrachloride gave 2.7 g of 5-(2-hydroxy-3-bromo)propoxy-1-methyl-3,4-dihydrocarbostyril having a melting point of 155°–157° C. as colorless amorphous crystals.

EXAMPLE 9

Preparation of Compound of Formula II

To a solution of 5.0 g of 1-benzyl-3,4,5,6,7,8-hexahydrocarbostyril-5-one dissolved in 60 ml of chloroform were added 2.9 g of 3-chloro-1,2-propanediol and 3.5 g of N-bromosuccinimide. The resulting solution was heated at reflux for 2 hours on a water bath, and thereafter worked up in the same manner as described in Example 8 to crystallize the crude product. Recrystallization of the product from carbon tetrachloride yielded 3.7 g of 1-benzyl-5-(2-hydroxy-3-chloro)propoxy-3,4-dihydrocarbostyril having a melting point of 105°–107° C. as colorless amorphous crystals.

In the same manner as described in Example 8, the following compounds were prepared:

5-(2-hydroxy-3-bromo)propoxy-3,4-dihydrocarbostyril, m.p., 133°–135° C. (recrystallized from ether), 5-(2-hydroxy-3-chloro)propoxy-1-methyl-3,4-dihydrocarbostyril, m.p., 137°–139° C. (recrystallized from carbon tetrachloride), 1-ethyl-5-(2-hydroxy-3-chloro)propoxy-3,4-dihydrocarbostyril, m.p., 117°–119° C. (recrystallized from carbon tetrachloride), 1-ethyl-5-(2-hydroxy-3-bromo)propoxy-3,4-dihydrocarbostyril, m.p., 115°–117.5° C. (recrystallized from carbon tetrachloride), 1-allyl-5-(2-hydroxy-3-chloro)propoxy-3,4-dihydrocarbostyril, m.p., 65°–67° C. (recrystallized from carbon tetrachloride), and 1-allyl-5-(2-hydroxy-3-bormo)propoxy-3,4-dihydrocarbostyril, m.p., 82°–84° C. (recrystallized from carbon tetrachloride).

EXAMPLE 10

Preparation of Compound of Formula I 2.0 g of 5-(2,3-epoxy)propoxy-3,4-dihydrocarbostyril and 6.5 g of benzylamine were added to 40 ml of ethanol, and the resulting mixture was stirred for a period of 4 hours. The reaction mixture was then distilled under reduced pressure to remove ethanol and unreacted benzylamine. The resulting residue was dissolved in acetone and an ethanolic solution of hydrogen chloride was added thereto. The precipitated crystals were then separated by filtration and recrystallized from methanol to obtain 1.7 g of 5-(2-hydroxy-3-benzylamino)propoxy-3,4-dihydrocarbostyril hydrochloride having a melting point of 210°–212° C. as a colorless amorphous solid.

EXAMPLE 11

Preparation of Compound of Formula I 1.0 g of 5-(2,3-epoxy)propoxy-3,4-dihydrocarbostyril and 1.5 g of di-n-propylamine were added to 30 ml of ethanol, and the resulting mixture was stirred at a temperature of from 50° to 55° C. for 4 hours. The reaction mixture was then distilled under reduced pressure to remove ethanol and unreacted dipropylamnine. The thus obtained residue was dissolved in acetone and an ethanolic solution of hydrogen chloride was added thereto to form crystals which were then separated by filtration and recrystallized from ethanol to obtain 0.7 g of 5-(2-hydroxy-3-di-n-propylamino)propoxy-3,4-dihydrocarbostyril having a melting point of 221°–222° C. as colorless amorphous crystals.

EXAMPLE 12

Preparation of Compound of Formula I 3.0 g of 5-(2,3-epoxy)propoxy-3,4-dihydrocarbostyril and 6.0 g of cyclohexylamine were added to 40 ml of methanol, and the resulting mixture was stirred at a temperature of from 55° to 60° C. for 3 hours. After allowing the mixture to cool, the precipitated crystals were separated by filtration, washed with acetone and then recrystallized from methanol to yield 3.5 g of 5-(2-hydroxy-3-cyclohexylamino)propoxy-3,4-dihydrocarbostyril as a colorless amorphous solid. The thus obtained product was dissolved in 100 ml of ethanol and 2 g of fumaric acid was added thereto. The mixture was stirred to form crystals which were then separated by filtration and recrystallized from ethanol to yield 4.2 g of 5-(2-hydroxy-3-cyclohexylamino)propoxy-3,4-dihydrocarbostyril fumarate having a melting point of 200°–202° C. as a colorless amorphous solid.

EXAMPLE 13

2.0 g of 5-(2,3-epoxy)propoxy-3,4-dihydrocarbostyril and 5.0 g of diisobutylamine were added to 30 ml of tetrahydrofuran. The reaction mixture was then worked up in the same manner as described in Example 12 to produce the crude crystals. Recrystallization of the product from acetone yielded 1.4 g of 5-(2-hydroxy-3-diisobutylamino)propoxy-3,4-dihydrocarbostyril hydrochloride having a melting point of 190°–192° C. as a colorless amorphous solid.

EXAMPLE 14

2.0 g of 5-(2-hydroxy-3-chloro)propoxy-3,4-dihydrocarbostyril and 5 g of tert.-butylamine were added to 30 ml of dioxane, and the resulting reaction mixture was heated at reflux for a period of 3 hours with stirring. After completion of the reaction, dioxane and unreacted tert.-butylamine were distilled off from the mixture under reduced pressure. To the resulting residue was added a methanolic hydrogen chloride followed by the addition of acetone. The precipitated crystals were separated by filtration and recrystallized from methanol-acetone to give 1.3 g of 5-(2-hydroxy-3-tert.-butylamino)propoxy-3,4-dihydrocarbostyril hydrochloride having a melting point of 277°–278° C. (with decomposition) as a colorless amorphous solid.

EXAMPLE 15

1.5 g of 5-(2-hydroxy-3-chloro)propoxy-3,4-dihydrocarbostyril and 2.5 g of isopropylamine were added to 25 ml of methanol, and the resulting reaction mixture was heated at reflux for 3 hours with stirring. After completion of the reaction, methanol and unreacted iso-propylamine were removed by distillation under reduced pressure. The resulting residue was dissolved in acetone and iso-propanol containing hydrogen chloride was added thereto to form precipitates which were then separated by filtration. Recrystallization of the precipitates from methanol-acetone gave 1.1 g of 5-(2-hydroxy-3-iso-propylamino)propoxy-3,4-dihydrocarbostyril hydrochloride having a melting point of 224°–225° C. as a colorless amorphous solid.

EXAMPLE 16

1.5 g of 1-methyl-5-(2,3-epoxy)propoxy-3,4-dihydrocarbostyril and 2.0 g of tertbutylamine were added to 30 ml of benzene, and the resulting mixture was stirred at a temperature of from 55° to 60° C. for 4 hours. After completion of the reaction the reaction mixture was distilled under reduced pressure to remove benzene and unreacted tert.-butylamine to give a residue. The residue was then dissolved in acetone and a solution of maleic acid in acetone was added thereto, thereby crystallizing the product which was then filtered off. Recrystallization of the product from ethanol gave 1.3 g of 1-methyl-5-(2-hydroxy-3-tert.-butylamino)propoxy-3,4-dihydrocarbostyril maleate having a melting point of 160°–163° C. as a colorless amorphous solid.

EXAMPLE 17

1.0 g of 1-ethyl-5-(2,3-epoxy)propoxy-3,4-dihydrocarbostyril and 2 g of isopropylamine were added to 20 ml of toluene, and the resulting reaction mixture was stirred at a temperature of from 50° to 55° C. for 5 hours. After completion of the reaction, toluene and unreacted isopropylamine were removed from the mixture by distillation under reduced pressure. The resulting residue was dissolved in acetone and isopropanol containing hydrogen chloride was added thereto to crystallize the product which was then filtered off. Recrystallization of the product from ethanol yielded 0.85 g of 1-ethyl-5-(2-hydroxy-3-isopropylamino)-propoxy-3,4-dihydrocarbostyril hydrochloride having a melting point of 154.5°–156.5° C. as a colorless amorphous solid.

EXAMPLE 18

1.3 g of 1-allyl-5-(2,3-epoxy)propoxy-3,4-dihydrocarbostyril and 1.5 g of tertbutylamine were added to 30 ml of ethanol, and the resulting reaction mixture was stirred at a temperature of from 60° to 65° C. for 4 hours. After completion of the reaction, ethanol and unreacted tertbutylamine were distilled off and the resulting residue was dissolved in acetone. To this was added a solution of fumaric acid in methanol to crystallize the product which was then separated by filtration. Recrystallization of the product from ethanol gave 1.0 g of 1-allyl-5-(2-hydroxy-3-tertbutylamino)propoxy-3,4-dihydrocarbostyril fumarate having a melting point of 209°–210° C. as a colorless amorphous solid.

EXAMPLE 19

2.0 g of 1-benzyl-5-(2,3-epoxy)propoxy-3,4-dihydrocarbostyril and piperidine were added to 30 ml of dimethylformamide, and the resulting mixture was stirred at a temperature of from 60° to 65° C. for 4 hours. After completion of the reaction, the reaction mixture was worked up in the same manner as described in Example 10 to obtain 1.2 g of 1-benzyl-5-(2-hydroxy-3-piperidino)propoxy-3,4-dihydrocarbostyril hydrochloride having a melting point of 216.5°–218.5° C. as colorless amorphous crystals.

EXAMPLE 20

1.5 g of 1-methyl-5-(2-hydroxy-3-chloro)propoxy-3,4-dihydrocarbostyril and 3.0 g of isopropylamine were added to 20 ml of ethanol, and the resulting mixture was heated at reflux for 4 hours. Thereafter, the reaction mixture was distilled under reduced pressure to remove ethanol and unreacted isopropylamine. To the resulting residue was added a methanolic hydrogen chloride followed by addition of acetone and the precipitated crystals were recrystallized from a methanol-acetone mixture to obtain 1.4 g of 1-methyl-5-(2-hydroxy-3-iso-propylamino)propoxy-3,4-dihydrocarbostyril hydrochloride having a melting point of 157°–159° C. as colorless needle crystals.

EXAMPLE 21

2.0 g of 1-ethyl-5-(2-hydroxy-3-chloro)propoxy-3,4-dihydrocarbostyril and 4.0 g of tertbutylamine were added to 20 ml of methanol, and the resulting mixture was heated at reflux for 6 hours. Thereafter, the mixture was distilled under reduced pressure to remove methanol and unreacted tertbutylamine. To the resulting residue was added methanolic hydrogen chloride followed by addition of acetone to form precipitates. Recrystallization of the precipitates yielded 1.5 g of 1-ethyl-5-(2-hydroxy-3-tertbutylamino)propoxy-3,4-dihydrocarbostyril hydrochloride having a melting point of 181°–183° C. as a colorless amorphous solid.

EXAMPLE 22

2.5 g of 1-benzyl-5-(2,3-epoxy)propoxy-3,4-dihydrocarbostyril and 2 g of isopropylamine were added to 40 ml of ethanol, and the resulting mixture was stirred at a temperature of from 60° to 65° C. for 4 hours. Thereafter, ethanol and unreacted isopropylamine were distilled off from the mixture under reduced pressure. The resulting residue was dissolved in acetone and ethanolic hydrogen chloride was added thereto. The precipitated crystals were separated by filtration and recrystallized from ethanol to give 1.8 g of 1-benzyl-5-(2-hydroxy-3-isopropylamino)propoxy-3,4-dihydrocarbostyril hydrochloride having a melting point of 192°–194° C. as a colorless amorphous solid.

EXAMPLE 23

1.5 g of 1-allyl-5-(2,3-epoxy)propoxy-3,4-dihydrocarbostyril and 2.0 g of secbutylamine were added to 30 ml of benzene, and the resulting mixture was worked up in the same manner as described in Example 22 to give crude crystals. Recrystallization of the crude crystals from ethanol yielded 1.1 g of 1-allyl-5-(2-hydroxy-3-secbutylamino)propoxy-3,4-dihydrocarbostyril fumarate having a melting point of 183°–184.5° C. as a colorless amorphous solid.

EXAMPLES 24–54

In the same manner as described in the above described Examples, the following compounds were prepared:

TABLE 1

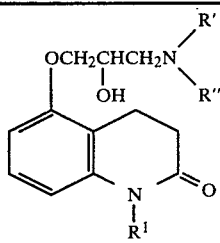

| Example | $R^1$ | R' | R'' | A | Recrystallization Solvent | Crystal Form | m.p. (°C.) |
|---|---|---|---|---|---|---|---|
| 24 | H | H | —CHCH$_3$(C$_2$H$_5$) | HCl | Ethanol | Amorphous Solid | 228–31 |
| 25 | H | H | —CH$_2$CH(CH$_3$)$_2$ | CHCOOH ‖ CHCOOH | Ethanol | Amorphous Solid | 194–6 |
| 26 | H | H | —(CH$_2$)$_3$CH$_3$ | HCl | Ethanol-Methanol | Amorphous Solid | 203–5 |
| 27 | H | H | —⟨ ⟩ | HCl | Ethanol | Colorless Needles | 251–3 |
| 28 | H | —CH(CH$_3$)$_2$ | —CH(CH$_3$)$_2$ | HCl | Isopropanol | Colorless Amorphous Solid | 208–10 |
| 29 | H | —CH$_3$ | —CH$_3$ | CHCOOH ‖ CHCOOH | Isopropanol | Colorless Amorphous Solid | 139–40 |

TABLE 1-continued

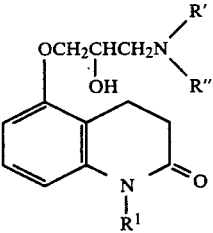

| | R¹ | R' | R'' | | Solvent | | m.p. (°C) |
|---|---|---|---|---|---|---|---|
| 30 | H | —CH₃ | cyclohexyl | CHCOOH<br>‖<br>CHCOOH | Iso-propanol | Colorless Amorphous Solid | 136-8 |
| 31 | H | —CH₃ | —CH₂—phenyl | HOOCCH<br>‖<br>HCCOOH | Iso-propanol | Colorless Amorphous Solid | 181-3 |
| 32 | H | —CH₃ | —(CH₂)₃CH₃ | CHCOOH<br>‖<br>CHCOOH | Iso-propanol | Colorless Amorphous Solid | 121-3 |
| 33 | H | —(CH₂)₃CH₃ | —(CH₂)₃CH₃ | CHCOOH<br>‖<br>CHCOOH | Iso-propanol | Colorless Amorphous Solid | 139-40 |
| 34 | —CH₃ | H | —CHCH₃(C₂H₅) | CHCOOH<br>‖<br>CHCOOH | Acetone | Colorless Needles | 152-5 |
| 35 | —CH₃ | H | cyclohexyl | CHCOOH<br>‖<br>CHCOOH | Acetone | Colorless Amorphous Solid | 161-3 |
| 36 | —CH₂CH₃ | H | —(CH₂)₃CH | HCl | Ethanol | Colorless Amorphous Solid | 126-8 |
| 37 | —CH₂CH₃ | H | cyclohexyl | HCl | Ethanol | Colorless Needles | 185-6 |
| 38 | —CH₂CH₃ | H | —CH₂—phenyl | HCl | Ethanol | Colorless Amorphous Solid | 155-7 |
| 39 | —CH₂CH₃ | —CH₃ | —CH₂—phenyl | HCl | Acetone | Colorless Amorphous Solid | 216-7 |
| 40 | —CH₂—phenyl | —CH₃ | cyclohexyl | HCl | Ethanol | Colorless Amorphous Solid | 128-31 |
| 41 | —CH₂—phenyl | H | —C(CH₃)₃ | HCl | Methanol | Colorless Flakes | 192-3 |
| 42 | —CH₂CH═CH₂ | H | —CH(CH₃)₂ | HOOCCH<br>‖<br>HCCOOH | Ethanol | Colorless Amorphous Solid | 192-4 |
| 43 | H | H | —CH(CH₃)₂ | CHCOOH<br>‖<br>CHCOOH | Iso-propanol | Colorless Amorphous Solid | 177-8 |
| 44 | H | H | —C(CH₃)₃ | CHCOOH<br>‖<br>CHCOOH | Ethanol | Colorless Amorphous Solid | 206-7 |
| 45 | H | H | —C₂H₅ | CHCOOH<br>‖<br>CHCOOH | Iso-propanol | Colorless Amorphous Solid | 168-9 |
| 46 | H | H | —CHCH₃(C₂H₅) | CHCOOH<br>‖<br>CHCOOH | Ethanol | Colorless Needles | 142-4 |
| 47 | H | —CH₂CH(CH₃)₂ | —CH₂CH(CH₃)₂ | HCl | | | 190-192 |

TABLE 1-continued

Structure:
$$\text{OCH}_2\text{CHCH}_2\text{N}\diagdown \begin{matrix}R'\\R''\end{matrix}$$
with OH on the middle carbon, attached to a 3,4-dihydrocarbostyril ring system with N-R¹ and C=O.

| Example | R¹ | R' | R'' | A | Recrystallization Solvent | Crystal Form | m.p. (°C.) |
|---|---|---|---|---|---|---|---|
| 48 | H | —CH₃ | n-C₄H₉ | CHCOOH‖CHCOOH | | | 121–123 |
| 49 | —C₂H₅ | —CH₃ | —CH₂—⟨phenyl⟩ | | | | |
| 50 | H | \multicolumn{2}{piperidino (—N⟨CH₂CH₂CH₂CH₂CH₂⟩)} | CHCOOH‖CHCOOH | Methanol | Colorless Needles | 215–7 |
| 51 | H | morpholino (—N⟨...O⟩) | | CHCOOH‖CHCOOH | Methanol | Colorless Amorphous Solid | 252–4 |
| 52 | H | 4-methylpiperazino (—N⟨⟩N—CH₃) | | 2 · HCl | Methanol | Colorless Amorphous Solid | 256.5 (decomp.) |
| 53 | H | 2-methylpiperidino (—N⟨CH₃...⟩) | | HCl | Methanol | Colorless Amorphous Solid | 123–5 |
| 54 | —CH₂—⟨phenyl⟩ | 4-methylpiperazino (—N⟨⟩N—CH₃) | | 2 · HCl | Ethanol | Colorless Amorphous Solid | 247 (decomp.) |

EXAMPLE 55

2.0 g of 6-(2,3-epoxy)propoxy-3,4-dihydrocarbostyril and 4.5 g of tertbutylamine were added to 30 ml of methanol and the mixture was allowed to react for 4 hours at a temperature of from 50° to 60° C. The reaction mixture was distilled under reduced pressure to remove methanol and any excess of unreacted tert-butylamine, and the resulting residue was dissolved in acetone followed by addition of maleic acid. The precipitated crystals were separated by filtration and recrystallized from ethanol to give 1.5 g of 6-(2-hydroxy-3-tert.-butylamino)propoxy-3,4-dihydrocarbostyril maleate as a colorless solid having a melting point of 163°–166° C.

EXAMPLE 56

2.5 g of 7-(2,3-epoxy)propoxy-3,4-dihydrocarbostyril and 5.0 g of isopropylamine were added to 60 ml of ethanol and the mixture was allowed to react for 8 hours at a temperature of from 40° to 50° C. The reaction mixture was distilled under reduced pressure to remove ethanol and any excess of unreacted isopropylamine, and the resulting residue was dissolved in acetone followed by addition of isopropanol containing hydrogen chloride. The precipitated crystals were separated by filtration and recrystallized from ethanol to give 1.7 g of 7-(2-hydroxy-3-iso-propylamino)propoxy-3,4-dihydrocarbostyril hydrochloride as a colorless solid having a melting point of 207°–209° C. Melting point of the free compound: 147°–149° C. (recrystallized from acetone).

EXAMPLE 57

1.8 g of 8-(2-hydroxy-3-chloro)propoxy-3,4-dihydrocarbostyril and 3.5 g of iso-propylamine were added to 30 ml of isopropanol and the mixture was allowed to react for 5 hours at reflux. The reaction mixture was distilled under reduced pressure to remove isopropanol and any excess of unreacted isopropylamine, and the resulting residue was dissolved in acetone followed by addition of iso-propanol containing hydrogen chloride. The precipitated crystals were separated by filtration and recrystallized from ethanol to give 0.7 g of 8-(2l-hydroxy-3-iso-propylamino)propoxy-3,4-dihydrocarbostyril hydrochloride as a colorless solid having a melting point of 230°–232° C. The corresponding free compound had a melting point of 157°–159° C. after recrystallized from acetone.

In the same manner as described above, the following compounds were prepared:

6-(2-hydroxy-3-isopropylamino)propoxy-3,4-dihydrocarbostyril fumarate, m.p., 242°–245° C. (recrystallized from acetone), 7-(2-hydroxy-3-tertbutylamino)propoxy-3,4-dihydrocarbostyril hydrochloride, m.p., 251°–253° C. (recrystallized from ethanol), (melting point of the free compound: 122°–125° C. after recrystallized from acetone), and 8-(2-hydroxy-3-tertbutylamino)propoxy-3,4-dihydrocarbostyril hydrochloride, m.p., 236°–238° C. (recrystallized from ethanol), (melting point of the free compound: 158°–161° C. after recrystallized from acetone).

EXAMPLE 58

0.5 g of 5-(2-hydroxy-3-isopropylamino)propoxycarbostyril was dissolved in 100 ml of ethanol, and the solution was charged into an autoclave together with Raney nickel (0.5 g). The mixture was then shaken at a hydrogen pressure of 50 atms. at a temperature of from 40° to 50° C. for 5 hours. After completion of the reaction, the catalyst was filtered off, and the filtrate was distilled to remove ethanol. Recrystallization of the residue from isopropanol gave 0.48 g of 5-(2-hydroxy-3-isopropylamino)propoxy-3,4-dihydrocarbostyril as colorless amorphous crystals having a melting point of 144°–145.5° C.

Analysis: Calcd. for $C_{15}H_{22}N_2O_3$: C, 64.72; H, 7.79; N, 10.06. Found: C, 64.83; H, 8.12; N, 10.19.

EXAMPLE 59

0.5 g of 5-(2-hydroxy-3-tertbutylamino)propoxycarbostyril hydrochloride was dissolved in 500 ml of ethanol and the solution was charged into an autoclave together with Raney nickel (0.5 g). The mixture was then worked up in the same manner as Example 58 to give 0.47 g of 5-(2-hydroxy-3-tertbutylamino)propoxy-3,4-dihydrocarbostyril hydrochloride as colorless amorphous crystals having a melting point of 278° C. (with decomposition, recrystallized from ethanol).

Analysis: Calcd. for $C_{16}H_{25}N_2O_3Cl$: C, 58.44; H, 7.65; N, 8.50. Found: C, 58.21; H, 7.80; N, 8.54.

EXAMPLE 60

To 0.5 g of 5-(2-hydroxy-3-isopropylamino)propoxycarbostyril were added 0.01 g of palladium black and 10 ml of glacial acetic acid, and the mixture was shaken at a hydrogen pressure of 10 atms. at room temperature for 5 hours. After completion of the reaction, the catalyst was filtered off and the filtrate was distilled to remove glacial acetic acid. Water was added to the residue, and the aqueous solution was rendered alkaline with ammonia. The precipitated crystals were separated by filtration and recrystallized from iso-propanol to give 0.47 g of 5-(2-hydroxy-3-iso-propylamino)propoxy-3,4-dihydrocarbostyril.

EXAMPLE 61

2.0 g of 5-(2-hydroxy-3-tertbutylamino)propoxy-3,4-dihydrocarbostyril and 10 g of acetyl chloride were added to 30 ml of acetone followed by refluxing for 2 hours. After being allowed to stand overnight, the precipitated crystals were filtered, washed with acetone and recrystallized from methanol-acetone to give 1.7 g of 5-(2-acetoxy-3-tertbutylamino)propoxy-3,4-dihydrocarbostyril hydrochloride as a pale yellow amorphous solid having a melting point of 231° C. (with decomposition).

EXAMPLE 62

1.8 g of 5-(2-hydroxy-3-tertbutylamino)propoxy-3,4-dihydrocarbostyril and 0.3 g of sodium hydride were added to 50 ml of toluene, and the mixture was refluxed for 1 hour followed by the addition of 1 g of benzoyl chloride dissolved in 30 ml of toluene. The mixture was then refluxed for 4 hours and concentrated to dryness under reduced pressure. The resulting residue was dissolved in 150 ml of chloroform, and the chloroform solution was washed with 500 ml of water and dried over anhydrous sodium sulfate. The dried solution was distilled to remove chloroform, and the residue was dissolved in 50 ml of isopropanol. Hydrogen chloride gas was then bubbled into the solution, and the precipitated crystals were filtered and recrystallized from ethanol to give 1.5 g of 5-(2-benzoyloxy-3-tertbutylamino)propoxy-3,4-dihydrocarbostyril hydrochloride as a colorless amorphous solid having a melting point of 207°–209° C. (with decomposition).

EXAMPLE 63

1.5 g of 5-(2-hydroxy-3-isopropylamino)propoxy-3,4-dihydrocarbostyril and 1 g of acetyl chloride were added to 30 ml of acetone and the mixture was refluxed for 2 hours. After allowing the mixture to cool, the mixture was concentrated to dryness, and the residue was dissolved in water. The solution was rendered alkaline with aqueous ammonia and extracted with ethyl acetate. The extract was dried over anhydrous sodium sulfate and distilled to remove ethyl acetate. To a solution of the residue dissolved in acetone was added an ethereal solution of oxalic acid, and the precipitated crystals were filtered to give 0.9 g of 5-(2-acetoxy-3-isopropyl)propoxy-3,4-dihydrocarbostyril hydrochloride as a colorless amorphous solid having a melting point of 196°–198° C. (with decomposition).

EXAMPLE 64

In the same manner as described in Example 63 but using 1.5 g of 5-(2-hydroxy-3-iso-propylamino)propoxy-1-methyl-3,4-dihydrocarbostyril, the crude product was obtained. Recrystallization of the product from ethanol-isopropyl yielded 1.1 g of 1-methyl-5-(2-acetoxy-3-iso-propylamino)propoxy-3,4-dihydrocarbostyril hydrochloride having a melting point of 194°–196° C. (with decomposition) as a colorless amorphous solid.

EXAMPLE 65

In the same manner as described in Example 63 but using 2.0 g of 1-benzyl-5-(2-hydroxy-3-tertbutylamino)propoxy-3,4-dihydrocarbostyril, the crude product was obtained. Recrystallization of the product from ethanol-acetone yielded 1.4 g of 1-benzyl-5-(2-acetoxy-3-tert-butylamino)propoxy-3,4-dihydrocarbostyril maleate having a melting point of 191°–193° C. as a colorless amorphous solid.

EXAMPLE 66

3.0 g of 5-(2-hydroxy-3-tertbutylamino)propoxy-3,4-dihydrocarbostyril and 0.1 g of sodium hydride were added to 60 ml of xylene, and the mixture was refluxed with stirring for 1 hour. To the reaction mixture was added dropwise a solution of 2.8 g of 3,4,5-trimethoxybenzoylchloride dissolved in 40 ml of xylene for a period of 1 hour. The resulting mixture was then refluxed with stirring for 4 hours followed by being concentrated to dryness under reduced pressure. The residue was dissolved in chloroform, washed with water and extracted with 3 N hydrochloric acid. The hydrochloric acid layer was separated, rendered alkaline with sodium hydroxide and then extracted with chloroform. The chloroform layer was distilled off. To a solution of the resulting residue in 60 ml of acetone was added maleic acid. The precipitated crystals were separated by filtration and recrystallized from methanol to give 2.1 g of 5-[3-tertbutylamino-2-(3,4,5-trimethoxy)benzoyloxy]propoxy-3,4-dihydrocarbostyril maleate having a melting point of 224°–226° C. (with decomposition) as a colorless amorphous solid.

EXAMPLE 67

In the same manner as described in Example 66 but using 3.0 g of 5-(2-hydroxy-3-iso-propylamino)-propoxy-3,4-dihydrocarbostyril, there was obtained 1.5 g of 5-[3-iso-propylamino-2-(3,4,5-trimethoxy)benzoyloxy]propoxy-3,4-dihydrocarbostyril maleate as colorless amorphous having a melting point of 186°–188° C. (with decomposition) after being recrystallized from ethanol.

Analysis: Calcd. for $C_{29}H_{36}N_2O_{11}$: C, 59.32; H, 6.25; N, 4.58. Found: C, 59.18; H, 6.16; N, 4.76.

EXAMPLE 68

A mixture of 2.0 g of 5-(2-hydroxy-3-tertbutylamino)-propoxy-3,4-dihydrocarbostyril and 7.7 g of butyl chloride was refluxed for 4 hours and concentrated to dryness under reduced pressure. Water was added to the residue and the resulting mixture was rendered alkaline with aqueous ammonium and extracted with ethyl acetate followed by being dried over anhydrous sodium sulfate. Ethyl acetate was then distilled off and the residue was dissolved in acetone. To this was added an ethereal solution of oxalic acid. The precipitated crystals were separated by filtration and recrystallized from water to obtain 1.1 g of 5-(2-butyryloxy-3-tert-butylamino)propoxy-3,4-dihydrocarbostyril oxalate having a melting point of 229.5° C. (with decomposition) as a colorless amorphous solid.

Analysis: Calcd. for $C_{22}H_{32}N_2O_8$: C, 58.39; H, 7.13; N, 6.19. Found: C, 58.16; H, 7.19; N, 6.16.

EXAMPLE 69

2.5 g of 5-(2-hydroxy-3-tertbutylamino)propoxy-1-methyl-3,4-dihydrocarbostyril and 0.35 g of sodium hydride were added to 60 ml of benzene, and the resulting mixture was refluxed with stirring for 1 hour. A solution of 1.0 g of butyryl chloride dissolved in 20 ml of benzene was then added to the reaction mixture. The mixture was refluxed with stirring for 4 hours and concentrated to dryness under reduced pressure. The residue was dissolved in ethyl acetate, washed with water and dried over anhydrous sodium sulfate followed by distillation of ethyl acetate. The residue was dissolved in acetone and exalic acid was added thereto. The precipitated crystals were separated by filtration and recrystallized from water to give 1.4 g of 5-(2-butyryloxy-3-tertbutylamino)propoxy-1-methyl-3,4-dihydrocarbostyril oxalate having a melting point of 207° C. (with decomposition) as a colorless amorphous solid.

Analysis: Calcd. for $C_{23}H_{34}N_2O_8$: C, 59.21; H, 7.35; N, 6.01. Found: C, 58.98; H, 7.40; N, 6.07.

In the same manner as described in the above-described examples, the following compounds were prepared:

5-(2-benzoyloxy-3-isopropylamino)propoxy-3,4-dihydrocarbostyril oxalate, m.p., 195°–197° C. (with decomposition) (recrystallized from methanol), 5-(2-iso- butyryl -3-tertbutylamino)propoxy-3,4-dihydrocarbostyril hydrochloride, m.p., 244°–245° C. (with decomposition) (recrystallized from methanol), 5-[3-tertbutylamino-2-(3,4,5-trimethoxy)benzoyloxy]-propoxy-1-methyl-3,4-dihydrocarbostyril hydrochloride, m.p., 216°–218° C. (with decomposition) (recrystallized from methanol), 1-benzyl-5-[3-isopropylamino-2-(3,4,5-trimethoxy)-benzoyloxy]propoxy-3,4-dihydrocarbostyril hydrochloride, m.p., 125° C. (with decomposition) (recrystallized from methanol), 1-benzyl-5-[3-tertbutylamino-2-(3,4,5-trimethoxy)benzyloxy]propoxy-3,4-dihydrocarbostryil hydrochloride, m.p., 192°–194° C. (with decomposition) (recrystallized from acetone), and 1-allyl-5-[3-isoproylamino-2-(3,4,5-trimethoxy)benzoyloxy]propoxy-3,4-dihydrocarbostryil fumarate, m.p., 185°–187° C. (with decomposition) (recrystallized from methanol).

EXAMPLE 70

In the same manner as described in Examples 61–69 the following compounds were prepared:

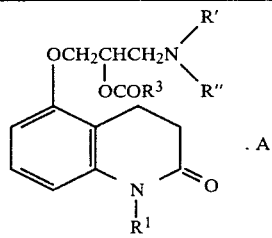

| $R^1$ | $R'$ | $R''$ | $R^3$ | A | Recrystallization Solvent | Crystal Form | Melting Point (°C.) |
|---|---|---|---|---|---|---|---|
| H | H | $CH(CH_3)_2$ | $CH_3$ | HCl | Methanol | Colorless Amorphous | 244–245 |
| H | H | $CH(CH_3)_2$ | $C(CH_3)_3$ | HCl | Iso- | Colorless | 234–236 |

-continued

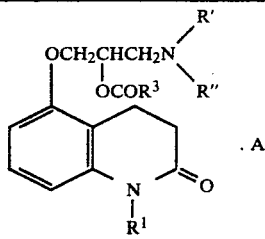

| R¹ | R' | R" | R³ | A | Recrystal-lization Solvent | Crystal Form | Melting Point (°C.) |
|---|---|---|---|---|---|---|---|
|   |   |   |   |   | propanol | Amorphous | (decomp.) |
| H | H | C(CH₃)₃ | C(CH₃)₃ | HCl | Iso-propanol | Colorless Amorphous | 210–212 (decomp.) |
| C₂H₅ | H | CH(CH₃)₂ | CH₃ | HCl | Ethyl Ether | Colorless Amorphous | 173–175 |
| H | H | C(CH₃)₃ | ⌬ | HCl | Ethanol | Colorless Amorphous | 207–209 |
| H | H | CH(CH₃)₂ | ⌬ | COOH\|COOH | Methanol | Colorless Amorphous | 195–197 |
| CH₃ | H | CH(CH₃)₂ | 3,4,5-tri-methoxy-phenyl | HCl | Methanol | Colorless Amorphous | 216–218 |

EXAMPLE 71

The antagonistic activity of the compounds of this invention against isopenaline was determined using the β-blockers screening method (C. E. Powell, I. H. Slater: J. Pharmac., 122, 480 (1958)).

Male hybrid adult dogs weighing 13 to 20 Kg were anesthesized with 30 mg/Kg of body weight of pentobarbital sodium administered intravenously. Each of the test compounds was then administered to the anesthesized dog at a dosage level of $10^{-7}$ mol/Kg of body weight from the femoral vein, and after 5 minutes isoprenaline was administered to the dog through the femoral vein at a dosage level of 0.3 γ/Kg of body weight. Blood pressure and the pulse (H.R.) were then recorded on a polygraph through a pressure transducer and a tachometer operated by the R wave of the electrocardiograph, respectively, to determine the % inhibitory activity of the test compound against the pulse increase and the pressure reduction induced by isoprenaline. The results obtained are shown in the Table below.

TABLE

| Test Compound* | Antagonistic Activity Against Isoprenaline (% Inhibitory)** | |
|---|---|---|
|  | Blood Pressure | Pulse |
| 1 | 8.9 | 9.3 |
| 2 | 35.7 | 12.8 |
| 3 | 35.3 | 12.7 |
| 4 | 44.4 | 32.6 |
| 5 | 94.4 | 53.2 |
| 6 | 46.8 | 25.6 |
| 7 | 40.0 | 20.4 |
| 8 | 27.6 | 10.8 |
| 9 | 75.4 | 35.1 |
| 10 | 23.7 | 5.5 |
| 11 | 36.9 | 0 |
| 12 | 100 | 82.8 |
| 13 | 76.5 | 55.6 |
| 14 | 13.3 | 10.0 |
| 15 | 65.9 | 67.5 |

*Test Compounds

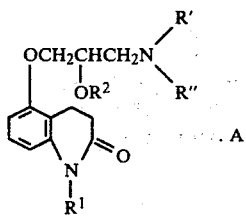

TABLE-continued

| No. | R¹ | R² | R' | R" | A |
|---|---|---|---|---|---|
| 1 | H | H | n-C₃H₇ | n-C₃H₇ | HCl |
| 2 | H | H | —CH₂—C₆H₅ | H | HCl & Maleate |
| 3 | H | H | —N(piperidino) | | HCl & Fumarate |
| 4 | —CH₃ | H | —CH(CH₃)₂ | H | HCl |
| 5 | —CH₃ | H | —C(CH₃)₃ | H | Maleate |
| 6 | —CH₂—C₆H₅ | H | —C(CH₃)₃ | H | HCl |
| 7 | —CHCH=CH₂ | H | —CH(CH₃)₂ | H | Fumarate |
| 8 | —CH₃ | —COCH₃ | —CH(CH₃)₂ | H | COOH COOH |
| 9 | H | —CO—C₆H₂(OCH₃)₃ | —C(CH₃)₃ | H | Maleate |

10

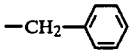

. Fumarate

11

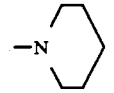

. HCl

12

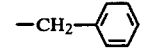

. HCl

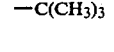

. A

| No. | R¹ | R' | R" | A |
|---|---|---|---|---|
| 13 | —C₂H₅ | —C(CH₃)₃ | H | HCl |
| 14 | —CHCH=CH₂ | —C(CH₃)₃ | H | Fumarate |
| 15 | —CH₂—C₆H₅ | —N(piperidino) | | HCl |

**The pulse increase and the pressure reduction induced by the administration of isoprenaline alone are referred to as 100%.

While the invention has been described in detail and with reference to specific embodiments thereof, it will be apparent to one skilled in the art that various changes and modifications can be made therein without departing from the spirit and scope thereof.

What is claimed is:

1. A 3,4-dihydrocarbostyril compound represented by the formula

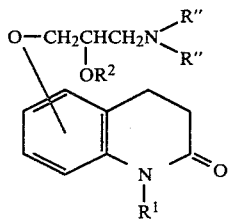

(I)

wherein $R^1$ is selected from the group consisting of hydrogen straight or branched alkyl having 1 to 4 carbon atoms, phenylalkyl wherein the alkyl has 1 to 4 carbon atoms, and alkenyl having 2 to 4 carbon atoms, $R^2$ is selected from the group consisting of hydrogen and acyl of the formula $COR^3$ wherein $R^3$ represents lower alkyl having 1 to 4 carbon atoms, phenyl or 3,4,5-trimethoxy phenyl, and $R'$ and $R''$ may be the same or different and each represents hydrogen, lower alkyl having 1 to 4 carbon atoms, phenylalkyl wherein the alkyl has 1 to 4 carbon atoms or cycloalkyl of 4 to 6 carbon atoms, or $R'$ and $R''$, when taken together with the nitrogen atom to which they are attached, may form a heterocyclic group selected from the group consisting of piperidino, piperazino and morpholino, said heterocyclic group being unsubstituted or substituted by alkyl of 1 to 4 carbon atoms, and pharmaceutically acceptable acid addition salts thereof, with the proviso that when substitution is at the 5-position and $R^1$ and $R^2$ are hydrogen and one of $R'$ and $R''$ is hydrogen, the other of $R'$ and $R''$ is not a 1 to 4 carbon atom alkyl group.

2. The compound of claim 1 wherein the heterocyclic group is N-methylpiperazino.

3. A 3,4-dihydrocarbostyril compound represented by the formula

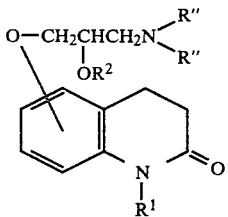

(I)

where $R^1$ is selected from the group consisting of hydrogen, straight or branched alkyl having 1 to 4 carbon atoms, phenylalkyl wherein the alkyl has 1 to 4 carbon atoms, and alkenyl having 2 to 4 carbon atoms, $R^2$ is hydrogen, and $R'$ and $R''$ may be the same or different and each represents hydrogen, lower alkyl having 1 to 4 carbon atoms, phenylalkyl wherein the alkyl has 1 to 4 carbon atoms or cycloalkyl of 4 to 6 carbon atoms or $R'$ and $R''$, when taken with the nitrogen atom to which they are attached may form a piperidino group, and pharmaceutically acceptable acid salts thereof, with the proviso that when substitution is as the 5-position and $R^1$ is hydrogen and one $R'$ and $R''$ is hydrogen, the other of $R'$ and $R''$ is not a 1 to 4 carbon atom alkyl group.

4. A 3,4-dihydrocarbostyril compound represented by the formula

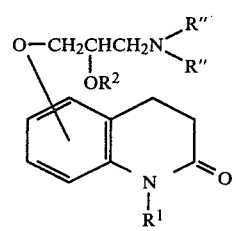

(I)

wherein $R^1$ is selected from the group consisting of hydrogen, straight or branched alkyl having 1 to 4 carbon atoms, phenylalkyl wherein the alkyl has 1 to 4 carbon atoms, and alkenyl having 2 to 4 carbon atoms, $R^2$ is selected from the group consisting of hydrogen and acyl of the formula $COR^3$ wherein $R^3$ represents lower alkyl having 1 to 4 carbon atoms, phenyl or 3,4,5-trimethoxy phenyl, and $R'$ and $R''$ may be the same or different and each represents hydrogen, lower alkyl having 1 to 4 carbon atoms, phenylalkyl wherein the alkyl has 1 to 4 carbon atoms or cycloalkyl of 4 to 6 carbon atoms, or $R'$ and $R''$, when taken together with the nitrogen atom to which they are attached, may form a heterocyclic group selected from the group consisting of piperidino, piperazino and morpholino, said heterocyclic group being unsubstituted or substituted by alkyl of 1 to 4 carbon atoms, and pharmaceutically acceptable acid addition salts thereof, with the proviso that when $R^1$ and $R^2$ are hydrogen each of $R'$ and $R''$ is not hydrogen and is not a 1 to 4 carbon atom alkyl group.

5. A 3,4-dihydrocarbostyril compound represented by the formula (I)

where $R^1$ is selected from the group consisting of hydrogen, straight or branched alkyl having 1 to 4 carbon atoms, phenylalkyl wherein the alkyl has 1 to 4 carbon atoms, and alkenyl having 2 to 4 carbon atoms, $R^2$ is hydrogen, and $R'$ and $R''$ may be the same or different and each represents hydrogen, lower alkyl having 1 to 4 carbon atoms, phenylalkyl wherein the alkyl has 1 to 4 carbon atoms or cycloalkyl of 4 to 6 carbon atoms or $R'$ and $R''$, when taken with the nitrogen atom to which they are attached may form piperidino, and pharmaceutically acceptable acid salts thereof, with the proviso that when $R^1$ is hydrogen each of $R'$ and $R''$ is not hydrogen and is not a 1 to 4 carbon atoms alkyl group.

6. A 3,4-dihydrocarbostyril compound represented by the formula

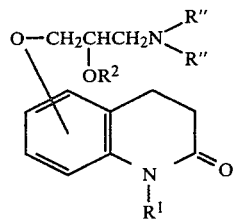

wherein R¹ is hydrogen, R² is hydrogen, substitution is at the 6-,7- or 8-position, and one of R' and R'' is hydrogen and the other of R' and R'' is 1 to 4 carbon atom alkyl.

7. A 3,4-dihydrocarbostyril compound represented by the formula

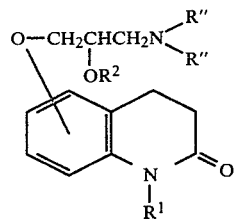

wherein R¹ is selected from the group consisting of straight or branched alkyl having 1 to 4 carbon atoms, phenylalkyl wherein the alkyl has 1 to 4 carbon atoms, and alkenyl having 2 to 4 carbon atoms, R² is selected from the group consisting of hydrogen and acyl of the formula COR³ wherein R³ represents lower alkyl having 1 to 4 carbon atoms, phenyl or 3,4,5-trimethoxy phenyl, and R' and R'' may be the same or different and each represents hydrogen, lower alkyl having 1 to 4 carbon atoms, phenylalkyl wherein the alkyl has 1 to 4 carbon atoms or cycloalkyl of 4 to 6 carbon atoms, or R' and R'', when taken together with the nitrogen atom to which they are attached, may form a heterocyclic group selected from the group consisting of piperidino, piperazino and morpholino, said heterocyclic group being unsubstituted or substituted by alkyl of 1 to 4 carbon atoms, and pharmaceutically acceptable acid addition salts thereof.

8. A 3,4-dihydrocarbostyril compound represented by the formula

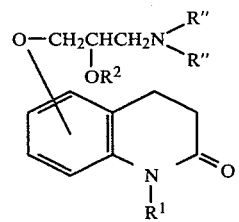

wherein R¹ is selected from the group consisting of hydrogen, straight or branched alkyl having 1 to 4 carbon atoms, phenylalkyl wherein the alkyl has 1 to 4 carbon atoms, and alkenyl having 2 to 4 carbon atoms, R² is selected from the group consisting of acyl of the formula COR³ wherein R³ represents lower alkyl having 1 to 4 carbon atoms, phenyl or 3,4,5-trimethoxy phenyl, and R' and R'' may be the same or different and each represents hydrogen, lower alkyl having 1 to 4 carbon atoms, phenylalkyl wherein the alkyl has 1 to 4 carbon atoms or cycloalkyl of 4 to 6 carbon atoms, or R' and R'', when taken together with the nitrogen atom to which they are attached, may from a heterocyclic group selected from the group consisting of piperidino, piperazino and morpholino, said heterocyclic group being unsubstituted or substituted by alkyl of 1 to 4 carbon atoms, and pharmaceutically acceptable acid addition salts thereof.

9. A 3,4-dihydrocarbostyril compound represented by the formula

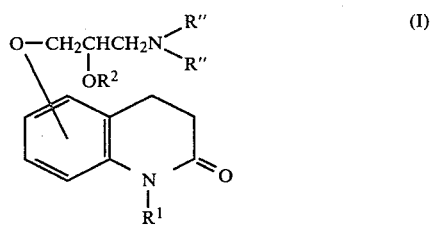

wherein R¹ is hydrogen, R² is selected from the group consisting of hydrogen and acyl of the formula COR³ wherein R³ represents lower alkyl having 1 to 4 carbon atoms, phenyl or 3,4,5-trimethoxy phenyl, and R' and R'' may be the same or different and each represents hydrogen, lower alkyl having 1 to 4 carbon atoms, phenylalkyl wherein the alkyl has 1 to 4 carbon atoms or cycloalkyl of 4 to 6 carbon atoms, or R' and R'', when taken together with the nitrogen atom to which they are attached, may form a heterocyclic group selected from the group consisting of piperidino, piperazino and morpholino, said heterocyclic group being unsubstituted or substituted by alkyl of 1 to 4 carbon atoms, and pharmaceutically acceptable acid addition salts thereof, with the proviso that when substitution is at the 5-position and R¹ and R² are hydrogen and one of R' and R'' is hydrogen, the other of R' and R'' is not a 1 to 4 carbon atom alkyl group.

10. A 3,4-dihydrocarbostyril compound represented by the formula

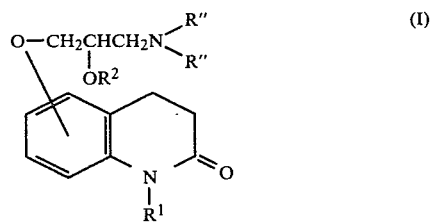

wherein R¹ is selected from the group consisting of hydrogen, straight or branched alkyl having 1 to 4 carbon atoms, phenylalkyl wherein the alkyl has 1 to 4 carbon atoms, and alkenyl having 2 to 4 carbon atoms, R² is hydrogen, and R' and R'' may be the same or different and each represents hydrogen, lower alkyl having 1 to 4 carbon atoms, phenylalkyl wherein the alkyl has 1 to 4 carbon atoms or cycloalkyl of 4 to 6 carbon atoms, or R' and R'', when taken together with the nitrogen atom to which they are attached, may form a heterocyclic group selected from the group consisting of piperidino, piperazino and morpholino, said heterocyclic group being unsubstituted or substituted by alkyl of 1 to 4 carbon atoms, and pharmaceutically acceptable acid addition salts thereof, with the proviso that when substitution is at the 5-position and R¹ and R² are hydrogen and one of R' and R" is hydrogen, the other of R' and R" is not a 1 to 4 carbon atom alkyl group.

11. 1-Methyl-5-(2-hydroxy-3-tert.-butylamino)-propoxy-3,4-dihydrocarbostyril.

12. 1-Methyl-5-(2-hydroxy-3-isopropylamino)-propoxy-3,4-dihydrocarbostyril.

13. 1-Ethyl-5-(2-hydroxy-3-tert.-butylamino)-propoxy-3,4-dihydrocarbostyril.

14. 1-Ethyl-5-(2-hydroxy-3-isopropylamino)propoxy-3,4-dihydrocarbostyril.

15. 5-(2-Hydroxy-3-cyclohexylamino)propoxy-3,4-dihydrocarbostyril.

16. 5-[2-(3,4,5-Trimethoxy)benzoyloxy-3-tert.-butylamino]-propoxy-3,4-dihydrocarbostyril.

17. 5-[2-(3,4,5-Trimethoxy)benzoyloxy-3-isopropylamino]-propoxy-3,4-dihydrocarbostyril.

18. 8-(2-Hydroxy-3-tert.-butylamino)propoxy-3,4-dihydrocarbostyril.

19. 8-(2-Hydroxy-3-isopropylamino)propoxy-3,4-dihydrocarbostyril.

20. 1-Allyl-5(2-hydroxy-3-tert.-butylamino)propoxy-3,4-dihydrocarbostyril.

21. 1-Allyl-5(2-hydroxy-3-isopropylamino)propoxy-3,4-dihydrocarbostyril.

22. 1-Benzyl-5(2-hydroxy-3-tert.-butylamino)-propoxy-3,4-dihydrocarbostyril.

* * * * *